United States Patent
Nakamoto et al.

(10) Patent No.: US 6,229,019 B1
(45) Date of Patent: May 8, 2001

(54) PHOSPHINOPYRROLINE COMPOUNDS AND PROCESS FOR PRODUCING THE SAME

(75) Inventors: Shin-ichi Nakamoto, Toyama; Kazuo Achiwa, 15-5, Kamikutsunoya-cho, Shizuoka-shi, Shizuoka 420-0815, both of (JP)

(73) Assignees: Fuji Yakuhin Kogyo Kabushiki Kaisha, Toyama; Kazuo Achiwa, Shizuoka, both of (JP)

( * ) Notice: Subject to any disclaimer, the term of this patent is extended or adjusted under 35 U.S.C. 154(b) by 0 days.

(21) Appl. No.: 09/319,007
(22) PCT Filed: Nov. 27, 1997
(86) PCT No.: PCT/JP97/04334
  § 371 Date: Jun. 17, 1999
  § 102(e) Date: Jun. 17, 1999
(87) PCT Pub. No.: WO98/23624
  PCT Pub. Date: Jun. 4, 1998

(30) Foreign Application Priority Data

Nov. 29, 1996 (JP) .................................................. 8-334673

(51) Int. Cl.$^7$ .............................. C07F 5/02; C07F 9/572; C07D 207/10
(52) U.S. Cl. ........................... 548/110; 548/111; 548/119; 548/405; 548/412; 548/413
(58) Field of Search .................................. 548/405, 412, 548/413, 110, 111, 119

(56) References Cited

U.S. PATENT DOCUMENTS

| 4,343,741 | 8/1982 | Townsend et al. | 548/412 |
| 4,539,411 | * 9/1985 | Broger et al. | 548/402 |
| 4,620,013 | * 10/1986 | Broger et al. | 548/412 |
| 4,668,795 | 5/1987 | Andrade et al. | 548/412 |
| 4,985,567 | * 1/1991 | Achiwa et al. | 548/412 |

FOREIGN PATENT DOCUMENTS

| 3302697 | * 8/1983 | (DE) | 548/412 |
| 0 185 882 A1 | 7/1986 | (EP) . | |
| 57-181093 | 11/1982 | (JP) . | |
| 60-166692 | 8/1985 | (JP) . | |
| 61-145192 | 7/1986 | (JP) . | |

* cited by examiner

*Primary Examiner*—Floyd D. Higel
(74) *Attorney, Agent, or Firm*—Wenderoth, Lind & Ponack, L.L.P.

(57) ABSTRACT

A process for producing phosphinopyrrolidine compounds especially useful for preparing optically active compounds through asymmetric synthesis which is a simplified short process requiring neither a step necessitating a high-temperature and high-pressure reaction nor special equipment for production. A phosphino group is incorporated into a pyrrolidine compound in the presence of a boron compound, and the resultant pyrrolidine compound is further reacted while protecting the phosphorous atom, whereby a dicyclohexylphosphino group can be efficiently incorporated into the pyrrolidine nucleus in the 4-position. Thus, the target phosphinopyrrolidine compounds useful as ligands for asymmetric synthesis catalysts can be obtained through a significantly small number of steps without resort to troublesome steps such as the step of reducing a phenyl group at high temperature and high pressure.

6 Claims, No Drawings

PHOSPHINOPYRROLINE COMPOUNDS AND PROCESS FOR PRODUCING THE SAME

This application is a 371 of PCT/JP97/04334 filed Nov. 27, 1997.

BACKGROUND OF THE INVENTION

1. Field of the Invention

The present invention relates to novel processes for producing phosphinopyrrolidine compounds which are chiral ligands for catalysts effective in asymmetric synthesis and to novel intermediate compounds which are products in the processes. Said processes enable us to simplify production steps including complicated multi-stages and further to make not only a manufacturing apparatus but also facilities for processes simple.

2. Description of the Related Art

Pantolactone is extensively utilized as a starting material for synthesizing pharmaceuticals, etc. Particularly, D-pantolactone (R-(-)-pantolactone) is well known as an intermediate in the preparation of D-pantothenic acid and pantethine which are useful as vitamins of medical or physiological importance. Since pantolactone has an asymmetric center in its molecule, chemically synthesized pantolactone products usually require optical resolution. In other words, D-pantolactone is prepared via the optical resolution of chemically synthesized D,L-pantolactone. Such a synthesis including the optical resolution is not only complicated and burdensome but also disadvantageous, such as costly. Specifically, the optical resolution has disadvantages in that it requires special agents, etc. and skills of operating it. That is, the process utilizing the optical resolution requires the use of expensive optical resolving agents such as quinine or brucine and further has defects in the recovery of D-pantolactone (it is not easy to recover D-pantolactone), etc. For means for solving these problems, a proposal of synthesizing optically active pantolactone by production processes utilizing an asymmetrically synthesizing reaction has been provided (U.S. Pat. No. 4,879,389).

For the process disclosed in U.S. Pat. No. 4,879,389, it has been reported that optically active pantolactone is prepared enantioselectively in quite excellent yields from an industrial standpoint by asymmetric hydrogenation using the phosphinopyrrolidine compounds; however, the synthesis of the phosphinopyrrolidine compounds, important reagents for the process, requires multi-processes including totally 14 steps, thereby incurring a drawback such as a demand for totally great expenditures. In the prior art process of synthesizing the phosphinopyrrolidine compounds, it is also essential to take a step of converting diphenylphosphino groups into dicyclohexylphosphino groups wherein benzene nuclei in the 4-diphenylphosphino are hydrogenated. The prior art hydrogenation conversion requires reactions at highly elevated temperatures and pressures (e.g., 150° C. and 150 atm), whereby there has been a drawback such as a demand for special facilities. Especially in industrial production, it is not easy to fit manufacturing facilities thereto. Further, such fitting facilities cost very much and are still accompanied with risks upon the manufacturing operation.

The phosphinopyrrolidine compounds are excellent reagents useful in catalytic asymmetric syntheses for not only pantolactone but also a wide variety of optically active compounds. Therefore, if it is feasible to synthesize the phosphinopyrrolidine compounds readily, efficiently, or unexpensively, it may enable us to apply such reagents to a diversity of asymmetric syntheses. Thus, to develop a production technique suited for these purposes is strongly demanded.

SUMMARY OF THE INVENTION

The present inventors have conducted an extensive research on synthesis of phosphinopyrrolidine compounds with aim of developing their simple and efficient production.

As a result, the present inventors have found that the reaction is conducted in the presence of boron compounds while blocking phosphorous atoms, whereby dicyclohexylphosphino groups protected with boron compounds can be efficiently introduced into position 4 of pyrrolidine nuclei, leading to formation of the desired phosphinopyrrolidine compounds useful for chiral ligands of catalysts in asymmetric synthesis, in extremely simple steps even without resort to processes including reduction of phenyl nuclei at highly elevated temperatures and pressures. Thus, the present invention is now provided.

The present invention provides:

(1) a process for producing a compound having the following formula (IV):

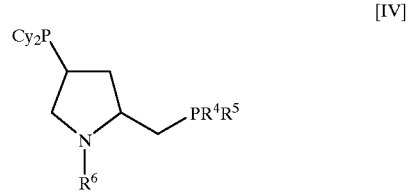

[IV]

wherein $R^4$ and $R^5$ which are identical or different, are independently an optionally substituted or unsubstituted aromatic hydrocarbon residue, and $R^6$ is hydrogen or a protecting group for an imino group, which comprises (i) reacting a compound having the following formula (I):

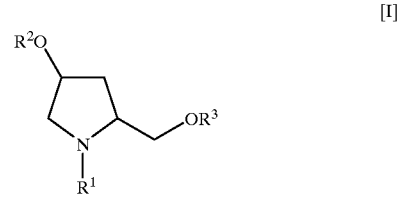

[I]

wherein $R^1$ is a protecting group for an imino group, $R^2$ and $R^3$ which are identical or different, are independently a protecting group for a hydroxy group, with a metal phosphine compound and a boron compound to form a compound having the following formula (II):

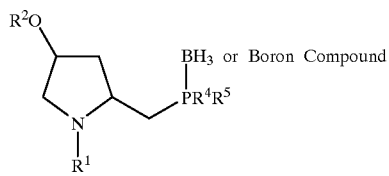

[II]

wherein $R^1$, $R^2$, $R^4$ and $R^5$ are as defined above,
(ii) then reacting the resultant compound (II) with a metal dicyclohexylphosphine compound and a boron compound to form a compound having the following formula (III):

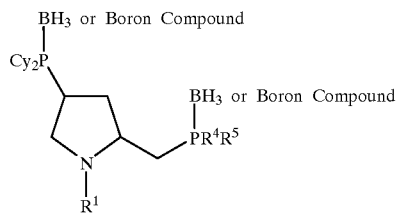

[III]

wherein $R^1$, $R^4$ and $R^5$ are as defined above,
(iii) decomplexing the resultant compound (III) for removal of the boron compound completed therewith to form the compound (IV);

(2) a compound of the formula (III) wherein $R^1$ is a protecting group for an imino group, $R^4$ and $R^5$ which are identical or different, are independently an optionally substituted or unsubstituted aromatic hydrocarbon residue, or a solvate thereof;

(3) a process for producing a compound of the formula (III) wherein $R^1$ is a protecting group for an imino group, $R^4$ and $R^5$ which are identical or different, are independently an optionally substituted or unsubstituted aromatic hydrocarbon residue,
which comprises
  (i) reacting a compound of the formula (II) wherein $R^2$ is a protecting group for a hydroxy group, and $R^1$, $R^4$ and $R^5$ are as defined above, with a metal dicyclohexylphosphine compound and a boron compound to form the compound (III);

(4) a compound of the formula (II) wherein $R^1$ is a protecting group for an imino group, $R^2$ is a protecting group for a hydroxy group, and $R^4$ and $R^5$ which are identical or different, are independently an optionally substituted or unsubstituted aromatic hydrocarbon residue, or a solvate thereof;

(5) a process for producing a compound of the formula (II) wherein $R^1$ is a protecting group for an imino group, $R^2$ is a protecting group for a hydroxy group, and $R^4$ and $R^5$ which are identical or different, are independently an optionally substituted or unsubstituted aromatic hydrocarbon residue, which comprises
  (i) reacting a compound of the formula (I) wherein $R^1$ is as defined above, $R^2$ and $R^3$ which are identical or different, are independently a protecting group for a hydroxy group, with a metal phosphine compound and a boron compound to form the compound (II); and (6) a process for producing a compound of the formula (IV) wherein $R^4$ and $R^5$ which are identical or different, are independently an optionally substituted or unsubstituted aromatic hydrocarbon residue, and $R^6$ is hydrogen or a protecting group for an imino group, which comprises
  (i) decomplexing a compound of the formula (III) wherein $R^1$ is a protecting group for an imino group, and $R^4$ and $R^5$ are as defined above, for removal of the boron compound complexed therewith to form the compound (IV).

In another aspect, the present invention provides:
(7) the process according to above (1), which comprises
  (i) reacting a compound of the formula (I) wherein $R^1$ is a group having an intervening carbonyl group or a group having an intervening sulfur atom, and $R^2$ and $R^3$ which are identical or different, are independently a group having an intervening sulfur atom, with a metal phosphine compound of the formula: $R^4R^5PM$ wherein $R^4$ and $R^5$ which are identical or different, are independently an optionally substituted or unsubstituted aromatic hydrocarbon residue wherein substituents on the aromatic hydrocarbon residue include alkyl, alkoxy, mono-, di-, or tri-alkyl-substituted amino, halogen, etc. (said aromatic hydrocarbon residue is hereinafter briefly referred to as "$R^{4a}$"), and M is metal, and borane or an alkyl derivative thereof to form a compound of the formula (II) wherein $R^1$, $R^2$, $R^4$ and $R^5$ have the same meanings as defined above,
  (ii) reacting the compound (II) with a metal dicyclohexylphosphine compound and borane or an alkyl derivative thereof to form a compound of the formula (III) wherein $R^1$, $R^4$ and $R^5$ have the same meanings as defined above,
  (iii) reacting the compound (III) with an agent selected from the group consisting of acids such as $CH_3SO_3H$, $CF_3SO_3H$, and $HBF_4 \cdot O(CH_3)_2$, and Lewis acids, leading to cleavage of P—B bonds, whereby a compound of the formula (IV) wherein $R^4$ and $R^5$ have the same meanings as defined above, and $R^6$ is hydrogen or as defined above for $R^1$, is formed;

(8) the process according to above (1), which comprises
  (i) reacting a compound of the formula (I) wherein $R^1$ is —CO—$R^{1a}$ wherein $R^{1a}$ is an optionally substituted or unsubstituted hydrocarbon residue, —COOR$^{1b}$ wherein $R^{1b}$ is an optionally substituted or unsubstituted hydrocarbon residue, —CONR$^{1c}$R$^{1d}$ wherein $R^{1c}$ and $R^{1d}$ which are identical or different, are independently hydrogen or an optionally substituted or unsubstituted hydrocarbon residue, or —S(O)$_n$R$^{1e}$ wherein $R^{1e}$ is an optionally substituted or unsubstituted hydrocarbon residue and n is an integer of 0, 1, or 2, and $R^2$ and $R^3$ which are identical or different, are independently —SO$_2$R$^{2a}$ wherein $R^{2a}$ is an optionally substituted or unsubstituted hydrocarbon residue, with a metal phosphine compound of the formula: $R^4R^5PM$ wherein $R^4$ and $R^5$ which are identical or different, are independently an optionally substituted or unsubstituted aryl wherein substituents on the aryl radical include alkyl, alkoxy, mono-, di-, or tri-alkyl-substituted amino, halogen, etc. (said aryl radical is hereinafter briefly referred to as "$R^{4b}$"), and M is metal, and borane or an alkyl derivative thereof to form a compound of the formula (II) wherein $R^1$, $R^2$, $R^4$ and $R^5$ have the same meanings as defined above,
  (ii) reacting the compound (II) with a metal dicyclohexylphosphine compound and borane or an alkyl derivative thereof to form a compound of the formula (III) wherein $R^1$, $R^4$ and $R^5$ have the same meanings as defined above, (iii) reacting the compound (III) with an agent selected from the group consisting of acids such as $CH_3SO_3H$, $CF_3SO_3H$ and $HBF_4.O(CH_3)_2$, and Lewis acids, leading to cleavage of P—B bonds, whereby a compound of the formula (IV) wherein $R^4$ and $R^5$ have the same meanings as defined above, and $R^6$ is hydrogen or as defined above for $R^1$, is formed; and (9) the process according to above (1), which comprises (i) reacting a compound of the formula (I) wherein $R^1$ is selected from the group consisting of alkoxycarbonyl having 2 to 7 carbon atoms, aryloxycarbonyl, aralkyloxycarbonyl and alkylcarbonyl having 2 to 6 carbon atoms, wherein "alkyl", "aryl", and "aralkyl" radicals may optionally contains one or more substituents selected from the group consisting of alkyl having 1 to 5 carbon atoms, alkoxy having 1 to 5 carbon atoms, nitro, halogen, hydroxy, and amino (said $R^1$ is hereinafter briefly referred to as "$R^{11}$"), and $R^2$ and $R^3$ which are identical or different, are independently selected from the group consisting of alkylsulfonyl having 1 to 6 carbon atoms and arylsulfonyl wherein "alkyl" and "aryl" radicals may optionally contains one or more substituents selected from the group consisting of alkyl having 1 to 5 carbon atoms, alkoxy having 1 to 5 carbon atoms, nitro, halogen, hydroxy, and amino (said $R^2$ and $R^3$ are hereinafter briefly referred to as "$R^{22}$", respectively), with a metal phosphine compound of the formula: $R^4R^5PM$ wherein $R^4$ and $R^5$ which are identical or different, are independently an optionally substituted or unsubstituted phenyl wherein substituents on the phenyl radical include lower alkyl having 1 to 5 carbon atoms, alkoxy having 1 to 5 carbon atoms, mono-, di-, or tri-$C_{1-5}$ alkyl-substituted amino, halogen, etc. (said phenyl radical is hereinafter briefly referred to as "$R^{4c}$"), and M is metal, and a member selected from the group consisting of borane, $BH_3.THF$, $BH_3.S(CH_3)_2$, borane complexes with amines wherein the amines are selected from the group consisting of $NH_3$, t-butylamine, dimethylamine, trialkylamine, morpholine, pyrrolidine, piperidine, pyridine, etc., borane derivatives (for example, $ThxBH_2$, $IpcBH_2$, $Ipc_2BH$, 9-BBN, $Sia_2BH$, $Cy_2BH$, catecholborane, etc.) and complexes of the borane derivatives with THF, $S(CH_3)_2$ or amines, to form a compound of the formula (II) wherein $R^1$, $R^2$, $R^4$ and $R^5$ have the same meanings as defined above, (ii) reacting the compound (II) with a metal dicyclohexylphosphine compound and a member selected from the group consisting of borane, $BH_3.THF$, $BH_3.S(CH_3)_2$, borane complexes with amines wherein the amines are selected from the group consisting of $NH_3$, t-butylamine, dimethylamine, trialkylamine, morpholine, pyrrolidine, piperidine, pyridine, etc., borane derivatives (for example, $ThxBH_2$, $IpcBH_2$, $Ipc_2BH$, 9-BBN, $Sia_2BH$, $Cy_2BH$, catecholborane, etc.) and complexes of the borane derivatives with THF, $S(CH_3)_2$ or amines, to form a compound of the formula (III) wherein $R^1$, $R^4$ and $R^5$ have the same meanings as defined above, (iii) reacting the compound (III) with an agent selected from the group consisting of acids such as $CH_3SO_3H$, $CF_3SO_3H$, and $HBF_4.O(CH_3)_2$, leading to cleavage of P—B bonds, whereby a compound of the formula (IV) wherein $R^4$ and $R^5$ have the same meanings as defined above, and $R^6$ is hydrogen or as defined above for $R^1$, is formed; and

(10) the process according to above (1), which comprises (i) reacting a compound of the formula (I) wherein $R^1$ is selected from the group consisting of t-butoxycarbonyl, benzyloxycarbonyl, acetyl, and p-methoxybenzyloxycarbonyl (said $R^1$ is hereinafter briefly referred to as "$R^{12}$"), and $R^2$ and $R^3$ which are identical or different, are independently selected from the group consisting of p-methylphenylsulfonyl (tosyl) and methylsulfonyl (mesyl) (said $R^2$ and $R^3$ are hereinafter briefly referred to as "$R^{23}$", respectively), with a metal phosphine compound of the formula: $R^4R^5PM$ wherein $R^4$ and $R^5$ which are identical or different, are independently an optionally substituted or unsubstituted phenyl wherein substituents on the phenyl radical include o-, m- or p-methoxy, 3,5-dimethyl-4-methoxy, 4-dimethylamino, 4-chloro, etc. (said phenyl radical is hereinafter briefly referred to as "$R^{4d}$"), and M is an alkali metal atom such as Li, Na and K, and a member selected from the group consisting of borane, $BH_3.THF$, $BH_3.S(CH_3)_2$, and borane complexes with amines wherein the amines are selected from the group consisting of $NH_3$, t-butylamine, dimethylamine, trialkylamine, morpholine, pyrrolidine, piperidine, pyridine, etc., to form a compound of the formula (II) wherein $R^1$, $R^2$, $R^4$ and $R^5$ have the same meanings as defined above, (ii) reacting the compound (II) with an alkaline metal dicyclohexylphosphine compound such as lithium dicyclohexylphosphine, and sodium dicyclohexylphosphine, and borane, to form a compound of the formula (III) wherein $R^1$, $R^4$ and $R^5$ have the same meanings as defined above, (iii) reacting the compound (III) with $HBF_4.O(CH_3)_2$, leading to cleavage of P—B bonds, whereby a compound of the formula (IV) wherein $R^4$ and $R^5$ have the same meanings as defined above, and $R^6$ is hydrogen or as defined above for $R^1$, is formed.

In yet another aspect, the present invention provides:

(11) the compound (III) according to above (2), wherein $R^1$ is a group having an intervening carbonyl group or a group having an intervening sulfur atom, and $R^4$ and $R^5$ have the same meanings as defined above for $R^{4a}$, or a solvate thereof;

(12) the compound (III) according to above (2), wherein $R^1$ is —CO—$R^{1a}$, —COO$R^{1b}$, —CONR$^{1c}R^{1d}$ or —S(O)$_nR^{1e}$ wherein $R^{1a}$, $R^{1b}$, $R^{1c}$, $R^{1d}$ and $R^{1e}$ have the same meanings as defined above, and n is an integer of 0, 1, or 2, and $R^4$ and $R^5$ have the same meanings as defined above for $R^{4b}$, or a solvate thereof;

(13) the compound (III) according to above (2), wherein $R^1$ has the same meaning as defined above for $R^{11}$ and $R^4$ and $R^5$ have the same meanings as defined above for $R^{4c}$, or a solvate thereof; and

(14) the compound (III) according to above (2), wherein $R^1$ has the same meaning as defined above for $R^{12}$, and $R^4$ and $R^5$ have the same meanings as defined above for $R^{4d}$, or a solvate thereof.

In a further aspect, the present invention provides:

(15) the process according to above (3), which comprises reacting a compound of the formula (II) wherein $R^1$ is a group having an intervening carbonyl group or a group having an intervening sulfur atom, $R^2$ is a group having an intervening sulfur atom, and $R^4$ and $R^5$ have the same meanings as defined above for $R^{4a}$, with a metal dicyclohexylphosphine compound and borane or an alkyl derivative thereof to form a compound of the formula (III) wherein $R^1$, $R^4$ and $R^5$ have the same meanings as defined above;

(16) the process according to above (3), which comprises reacting a compound of the formula (II) wherein $R^1$ is —CO—$R^{1a}$, —COOR$^{1b}$, —CONR$^{1c}R^{1d}$ or —S(O)$_nR^{1e}$ wherein $R^{1a}$, $R^{1b}$, $R^{1c}$, $R^{1d}$ and $R^{1e}$ have the same meanings as defined above, and n is an integer of 0, 1, or 2, $R^2$ is —SO$_2R^{2a}$ wherein $R^{2a}$ has the same meaning as defined above, and $R^4$ and $R^5$ have the same meanings as defined above for $R^{4b}$, with a metal dicyclohexylphosphine compound and borane or an alkyl derivative thereof to form a compound of the formula (III) wherein $R^1$, $R^4$ and $R^5$ have the same meanings as defined above;

(17) the process according to above (3), which comprises reacting a compound of the formula (II) wherein $R^1$ has the same meaning as defined above for $R^{11}$, $R^2$ has the same meaning as defined above for $R^{22}$, and $R^4$ and $R^5$ have the same meanings as defined above for $R^{4c}$, with a metal dicyclohexylphosphine compound and a member selected from the group consisting of borane, BH$_3$.THF, BH$_3$.S(CH$_3$)$_2$, borane complexes with amines wherein the amines are selected from the group consisting of NH$_3$, t-butylamine, dimethylamine, trialkylamine, morpholine, pyrrolidine, piperidine, pyridine, etc., borane derivatives (for example, ThxBH$_2$, IpcBH$_2$, Ipc$_2$BH, 9-BBN, Sia$_2$BH, Cy$_2$BH, catecholborane, etc.) and complexes of the borane derivatives with THF, S(CH$_3$)$_2$ or amines, to form a compound of the formula (III) wherein R $R^4$ and $R^5$ have the same meanings as defined above; and

(18) the process according to above (3), which comprises reacting a compound of the formula (II) wherein $R^1$ has the same meaning as defined above for $R^{12}$, $R^2$ has the same meaning as defined above for $R^{23}$, and $R^4$ and $R^5$ have the same meanings as defined above for $R^{4d}$, with a metal dicyclohexylphosphine compound and a member selected from the group consisting of borane, BH$_3$.THF, BH$_3$.S(CH$_3$)$_2$, and borane complexes with amines wherein the amine is selected from the group consisting of NH$_3$, t-butylamine, dimethylamine, trialkylamine, morpholine, pyrrolidine, piperidine, pyridine, etc., to form a compound of the formula (III) wherein $R^1$, $R^4$ and $R^5$ have the same meanings as defined above.

In still another aspect, the present invention provides:

(19) the compound (II) according to above (4), wherein $R^1$ is a group having an intervening carbonyl group or a group having an intervening sulfur atom, $R^2$ is a group having an intervening sulfur atom, and $R^4$ and $R^5$ have the same meanings as defined above for $R^{4a}$, or a solvate thereof;

(20) the compound (II) according to above (4), wherein $R^1$ is —CO—$R^{1a}$, —COOR$^{1b}$, —CONR$^{1c}R^{1d}$ or —S(O)$_nR^{1e}$ wherein $R^{1a}$, $R^{1b}$, $R^{1c}$, $R^{1d}$ and $R^{1e}$ have the same meanings as defined above, and n is an integer of 0, 1, or 2, $R^2$ is —SO$_2R^{2a}$ wherein $R^{2a}$ has the same meaning as defined above, and $R^4$ and $R^5$ have the same meanings as defined above for $R^{4b}$, or a solvate thereof;

(21) the compound (II) according to above (4), wherein $R^1$ has the same meaning as defined above for $R^{11}$ $R^2$ has the same meaning as defined above for $R^{22}$, and $R^4$ and $R^5$ have the same meanings as defined above for $R^{4c}$, or a solvate thereof; and

(22) the compound (II) according to above (4), wherein $R^1$ has the same meaning as defined above for $R^{12}$ $R^2$ has the same meaning as defined above for $R^{23}$, and $R^4$ and $R^5$ have the same meanings as defined above for $R^{4d}$, or a solvate thereof.

In yet another aspect, the present invention provides:

(23) the process according to above (5), which comprises reacting a compound of the formula (I) wherein $R^1$ is a group having an intervening carbonyl group or a group having an intervening sulfur atom, and $R^2$ and $R^3$ which are identical or different, are independently a group having an intervening sulfur atom, with a metal phosphine compound of the formula: $R^4R^5$PM wherein $R^4$ and $R^5$ have the same meanings as defined above for $R^{4a}$, and and M is metal, and borane or an alkyl derivative thereof to form a compound of the formula (II) wherein $R^1$, $R^2$, $R^4$ and $R^5$ have the same meanings as defined above;

(24) the process according to above (5), which comprises reacting a compound of the formula (I) wherein $R^1$ is —CO—$R^{1a}$, —COOR$^{1b}$, —CONR$^{1c}R^{1d}$ or —S(O)$_nR^{1e}$ wherein $R^1$ is $R^{1b}$, $R^{1c}$, $R^{1d}$ and $R^{1e}$ have the same meanings as defined above, and n is an integer of 0, 1, or 2, and $R^2$ and $R^3$ which are identical or different, are independently —SO$_2R^{2a}$ wherein $R^{2a}$ has the same meaning as defined above, with a metal phosphine compound of the formula: $R^4R^5$PM wherein $R^4$ and $R^5$ have the same meanings as defined above for $R^{4b}$, and and M is metal, and borane or an alkyl derivative thereof to form a compound of the formula (II) wherein $R^1$, $R^2$, $R^4$ and $R^5$ have the same meanings as defined above;

(25) the process according to above (5), which comprises reacting a compound of the formula (I) wherein $R^1$ has the same meaning as defined above for $R^{11}$, and $R^2$ and $R^3$ have the same meanings as defined above for $R^{22}$, with a metal phosphine compound of the formula: $R^4R^5$PM wherein $R^4$ and $R^5$ have the same meanings as defined above for $R^{4c}$, and M is an alkali metal atom such as Li, Na and K, and a member selected from the group consisting of borane, BH$_3$.THF, BH$_3$.S(CH$_3$)$_2$, borane complexes with amines wherein the amines are selected from the group consisting of NH$_3$, t-butylamine, dimethylamine, trialkylamine, morpholine, pyrrolidine, piperidine, pyridine, etc., borane derivatives (for example, ThxBH$_2$, IpcBH$_2$, Ipc$_2$BH, 9-BBN, Sia$_2$BH, Cy$_2$BH, catecholborane, etc.) and complexes of the borane derivatives with THF, S(CH$_3$)$_2$ or amines, to form a compound of the formula (II) wherein $R^1$, $R^2$, $R^4$ and $R^5$ have the same meanings as defined above; and

(26) the process according to above (5), which comprises reacting a compound of the formula (I) wherein $R^1$ has the same meaning as defined above for $R^{12}$, and $R^2$ and $R^3$ have the same meanings as defined above for $R^{23}$, with a metal phosphine compound of the formula: $R^4R^5$PM wherein $R^4$ and $R^5$ have the same meanings as defined above for $R^{4d}$, and M is an alkali metal atom such as Li, Na and K, and a member selected from the group consisting of borane, BH$_3$.THF, BH$_3$.S(CH$_3$)$_2$, and borane complexes with amines wherein the amines are selected from the group consisting of $NH_3$, t-butylamine, dimethylamine, trialkylamine, morpholine, pyrrolidine, piperidine, pyridine, etc., to form a compound of the formula (II) wherein $R^1$, $R^2$, $R^4$ and $R^5$ have the same meanings as defined above.

In still a further aspect, the present invention provides:

(27) the process according to above (6), which comprises reacting a compound of the formula (III) wherein $R^1$ is a group having an intervening carbonyl group or a group having an intervening sulfur atom, and $R^4$ and $R^5$ have the same meanings as defined above for $R^{4a}$, with an agent selected from the group consisting of acids such as $CH_3SO_3H$, $CF_3SO_3H$, and $HBF_4 \cdot O(CH_3)_2$, and Lewis acids, leading to cleavage of P—B bonds, whereby a compound of the formula (IV) wherein $R^4$ and $R^5$ have the same meanings as defined above, and $R^6$ is hydrogen or as defined above for $R^1$, is formed;

(28) the process according to above (6), which comprises reacting a compound of the formula (III) wherein $R^{1a}$, is —CO—$R^{1a}$, —COOR$^{1b}$, —CONR$^{1c}R^{1d}$ or —S(O)$_n$—R$^{1e}$ wherein $R^{1a}$, $R^{1b}$, $R^{1c}$, $R^{1d}$ and $R^{1e}$ have the same meanings as defined above, and n is an integer of 0, 1, or 2, and $R^4$ and $R^5$ have the same meanings as defined above for $R^{4b}$, with an agent selected from the group consisting of acids such as $CH_3SO_3H$, $CF_3SO_3H$, and $HBF_4 \cdot O(CH_3)_2$, and Lewis acids, leading to cleavage of P—B bonds, whereby a compound of the formula (IV) wherein $R^4$ and $R^5$ have the same meanings as defined above, and $R^6$ is hydrogen or as defined above for $R^1$, is formed;

(29) the process according to above (6), which comprises reacting a compound of the formula (III) wherein $R^1$ has the same meaning as defined above for $R^{11}$, and $R^4$ and $R^5$ have the same meanings as defined above for $R^{4c}$, with an agent selected from the group consisting of acids such as $CH_3SO_3H$, $CF_3SO_3H$, and $HBF_4 \cdot O(CH_3)_2$, leading to cleavage of P—B bonds, whereby a compound of the formula (IV) wherein $R^4$ and $R^5$ have the same meanings as defined above, and $R^6$ is hydrogen or as defined above for $R^1$, is formed; and

(30) the process according to above (6), which comprises reacting a compound of the formula (III) wherein $R^1$ has the same meaning as defined above for $R^{12}$, and $R^4$ and $R^5$ have the same meanings as defined above for $R^{4d}$, with $HBF_4 \cdot O(CH_3)_2$ for cleavage of P—B bonds to form a compound of the formula (IV) wherein $R^4$ and $R^5$ have the same meanings as defined above, and $R^6$ is hydrogen or as defined above for $R^1$.

In a further aspect, the present invention provides

(31) a process for producing a compound of the formula

[V]

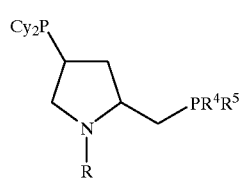

wherein $R^4$ and $R^5$ which are identical or different, are independently an optionally substituted or unsubstituted aromatic hydrocarbon residue, and R is a protecting group for an imino group, which comprises (i) reacting a compound of the formula (I) wherein $R^1$ is a protecting group for an imino group, and $R^2$ and $R^3$ which are identical or different, are independently a protecting group for a hydroxy group, with a metal phosphine compound and a boron compound to form a compound of the formula (II) wherein $R^1$, $R^2$, $R^4$ and $R^5$ have the same meanings as defined above, (ii) then reacting the resultant compound (II) with a metal dicyclohexylphosphine compound and a boron compound to form a compound of the formula (III) wherein $R^1$, $R^4$ and $R^5$ have the same meanings as defined above, (iii) decomplexing the resultant compound (III) for removal of the boron compound complexed therewith to form the compound (IV) wherein $R^4$ and $R^5$ have the same meanings as defined above, and $R^6$ is hydrogen or as defined above for $R^1$, and (iv) as required when the compound (IV) wherein $R^6$ is hydrogen is obtained, optionally introducing further thereinto a substituent R wherein R has the same meaning as defined above;

(32) the process according to above (31), which comprises (i) reacting a compound of the formula (I) wherein $R^1$ is a group having an intervening carbonyl group or a group having an intervening sulfur atom, and $R^2$ and $R^3$ which are identical or different, are independently a group having an intervening sulfur atom, with a metal phosphine compound of the formula: $R^4R^5PM$ wherein $R^4$ and $R^5$ have the same meanings as defined above for $R^{4a}$, and M is metal, and borane or an alkyl derivative thereof to form a compound of the formula (II) wherein $R^1$, $R^2$, $R^4$ and $R^5$ have the same meanings as defined above, (ii) reacting the compound (II) with a metal dicyclohexylphosphine compound and borane or an alkyl derivative thereof to form a compound of the formula (III) wherein $R^1$, $R^4$ and $R^5$ have the same meanings as defined above, (iii) reacting the compound (III) with an agent selected from the group consisting of acids such as $CH_3SO_3H$, $CF_3SO_3H$, and $HBF_4 \cdot O(CH_3)_2$, and Lewis acids, leading to cleavage of P—B bonds, whereby a compound of the formula (IV) wherein $R^4$ and $R^5$ have the same meanings as defined above, and $R^6$ is hydrogen or as defined above for $R^1$, is formed, (iv) as required when the compound (IV) wherein $R^6$ is hydrogen is obtained, optionally introducing further a substituent R wherein R is a group having an intervening carbonyl group or a group having an intervening sulfur atom thereinto to form a compound of the formula (V) wherein $R^4$, $R^5$ and R have the same meanings as defined above;

(33) the process according to above (31), which comprises (i) reacting a compound of the formula (I) wherein $R^1$ is —CO—$R^{1a}$, —COOR$^{1b}$, —CONR$^{1c}R^{1d}$ or —S(O)$_n$R$^{1e}$ wherein $R^{1a}$, $R^{1b}$, $R^{1c}$, $R^{1d}$ and $R^{1e}$ have the same meanings as defined above, and n is an integer of 0, 1, or 2, and $R^2$ and $R^3$ which are identical or different, are independently —SO$_2R^{2a}$ wherein $R^{2a}$ has the same meaning as defined above, with a metal phosphine compound of the formula: $R^4R^5PM$ wherein $R^4$ and $R^5$ have the same meanings as defined above for $R^{4b}$, and M is metal, and borane or an alkyl derivative thereof to form a compound of the formula (II) wherein $R^1$, $R^2$, $R^4$ and $R^5$ have the same meanings as defined above, (ii) reacting the compound (II) with a metal dicyclohexylphosphine compound and borane or an alkyl derivative thereof to form a compound of the formula (III) wherein $R^1$, $R^4$ and $R^5$ have the same meanings as defined above, (iii) reacting the compound (III) with an agent selected from the group consisting of acids such as $CH_3SO_3H$, $CF_3SO_3H$, and $HBF_4 \cdot O(CH_3)_2$, and Lewis acids, leading to cleavage of P—B bonds, whereby a compound of the formula (IV) wherein $R^4$ and $R^5$ have the same meanings as defined above, and $R^6$ is hydrogen or as defined above for $R^1$, is formed, (iv) as required when the compound (IV) wherein $R^6$ is hydrogen is obtained, optionally introducing further thereinto a substituent R wherein R is —CO—$R^{3a}$ wherein $R^{3a}$ is an optionally substituted or unsubstituted hydrocarbon residue, —COO$R^{3b}$ wherein $R^{3b}$ is an optionally substituted or unsubstituted hydrocarbon residue, —CON$R^{3c}R^{3d}$ wherein $R^{3c}$ and $R^{3d}$ which are identical or different, are independently hydrogen or an optionally substituted or unsubstituted hydrocarbon residue, —S(O)$_n R^{3e}$ wherein $R^{3e}$ is an optionally substituted or unsubstituted hydrocarbon residue, and n is an integer of 0, 1, or 2, to form a compound of the formula (V) wherein $R^4$, $R^5$ and R have the same meanings as defined above;

(34) the process according to above (31), which comprises (i) reacting a compound of the formula (I) wherein $R^1$ has the same meaning as defined above for $R^{11}$, and $R^2$ and $R^3$ have the same meanings as defined above for $R^{22}$, with a metal phosphine compound of the formula: $R^4R^5PM$ wherein $R^4$ and $R^5$ have the same meanings as defined above for $R^{4c}$, and M is an alkali metal atom such as Li, Na and K, and a member selected from the group consisting of borane, $BH_3 \cdot THF$, $BH_3 \cdot S(CH_3)_2$, borane complexes with amines wherein the amines are selected from the group consisting of $NH_3$, t-butylamine, dimethylamine, trialkylamine, morpholine, pyrrolidine, piperidine, pyridine, etc., borane derivatives (for example, ThxBH$_2$, IpcBH$_2$, Ipc$_2$BH, 9-BBN, Sia$_2$BH, Cy$_2$BH, catecholborane, etc.) and complexes of the borane derivatives with THF, S(CH$_3$)$_2$ or amines, to form a compound of the formula (II) wherein $R^1$, $R^2$, $R^4$ and $R^5$ have the same meanings as defined above, (ii) reacting the compound (II) with an alkaline metal dicyclohexylphosphine compound such as lithium dicyclohexylphosphine, and sodium dicyclohexylphosphine, and a member selected from the group consisting of borane, $BH_3 \cdot THF$, $BH_3 \cdot S(CH_3)_2$, borane complexes with amines wherein the amines are selected from the group consisting of $NH_3$, t-butylamine, dimethylamine, trialkylamine, morpholine, pyrrolidine, piperidine, pyridine, etc., borane derivatives (for example, ThxBH$_2$, IpcBH$_2$, Ipc$_2$BH, 9-BBN, Sia$_2$BH, Cy$_2$BH, catecholborane, etc.) and complexes of the borane derivatives with THF, S(CH$_3$)$_2$ or amines, to form a compound of the formula (III) wherein $R^1$, $R^4$ and $R^5$ have the same meanings as defined above, (iii) reacting the compound (III) with an agent selected from the group consisting of acids such as $CH_3SO_3H$, $CF_3SO_3H$, and $HBF_4 \cdot O(CH_3)_2$, and Lewis acids, leading to cleavage of P—B bonds, whereby a compound of the formula (IV) wherein $R^4$ and $R^5$ have the same meanings as defined above, and $R^6$ is hydrogen or as defined above for $R^1$, is formed, (iv) as required when the compound (IV) wherein $R^6$ is hydrogen is obtained, optionally introducing further thereinto a substituent R wherein R is selected from the group consisting of alkoxycarbonyl having 2 to 7 carbon atoms, aryloxycarbonyl, aralkyloxycarbonyl and alkylcarbonyl having 2 to 6 carbon atoms, wherein "alkyl", "aryl", and "aralkyl" residues may optionally contains one or more substituents selected from the group consisting of alkyl having 1 to 5 carbon atoms, alkoxy having 1 to 5 carbon atoms, nitro, halogen, hydroxy, and amino, to form a compound of the formula (V) wherein $R^4$, $R^5$ and R have the same meanings as defined above; and

(35) the process according to above (31), which comprises (i) reacting a compound of the formula (I) wherein $R^1$ has the same meaning as defined above for $R^{12}$, and $R^2$ and $R^3$ have the same meanings as defined above for $R^{23}$, with a metal phosphine compound of the formula: $R^4R^5PM$ wherein $R^4$ and $R^5$ have the same meanings as defined above for $R^{4d}$, and M is an alkali metal atom such as Li, Na and K, and a member selected from the group consisting of borane, $BH_3 \cdot THF$, $BH_3 \cdot S(CH_3)_2$, borane complexes with amines wherein the amines are selected from the group consisting of $NH_3$, t-butylamine, dimethylamine, trialkylamine, morpholine, pyrrolidine, piperidine, pyridine, etc., borane derivatives (for example, ThxBH$_2$, IpcBH$_2$, Ipc$_2$BH, 9-BBN, Sia$_2$BH, Cy$_2$BH, catecholborane, etc.) and complexes of the borane derivatives with THF, S(CH$_3$)$_2$ or amines, to form a compound of the formula (II) wherein $R^1$, $R^2$, $R^4$ and $R^5$ have the same meanings as defined above, (ii) reacting the compound (II) with an alkaline metal dicyclohexylphosphine compound such as lithium dicyclohexylphosphine, and sodium dicyclohexylphosphine, and a member selected from the group consisting of borane, $BH_3 \cdot THF$, $BH_3 \cdot S(CH_3)_2$, borane complexes with amines wherein the amines are selected from the group consisting of $NH_3$, t-butylamine, dimethylamine, trialkylamine, morpholine, pyrrolidine, piperidine, pyridine, etc., borane derivatives (for example, ThxBH$_2$, IpcBH$_2$, Ipc$_2$BH, 9-BBN, Sia$_2$BH, Cy$_2$BH, catecholborane, etc.) and complexes of the borane derivatives with THF, S(CH$_3$)$_2$ or amines, to form a compound of the formula (III) wherein $R^1$, $R^4$ and $R^5$ have the same meanings as defined above, (iii) reacting the compound (III) with $HBF_4 \cdot O(CH_3)_2$, leading to cleavage of P—B bonds, whereby a compound of the formula (IV) wherein $R^4$ and $R^5$ have the same meanings as defined above, and $R^6$ is hydrogen or as defined above for $R^1$, is formed, (iv) as required when the compound (IV) wherein $R^6$ is hydrogen is obtained, optionally introducing further thereinto a substituent R wherein R is selected from the group consisting of t-butoxycarbonyl, benzyloxycarbonyl, acetyl, and p-methoxybenzyloxycarbonyl, to form a compound of the formula (V) wherein $R^4$, $R^5$ and R have the same meanings as defined above.

In connection with the compounds of the present invention, there are carbon atoms of optically active centers at positions 2 and 4 of the pyrrolidine ring, and so there are possible stereoisomers, i.e., optical isomers (or enantiomers) and diastereomers, depending on each configuration. The combination of carbon configurations at positions 2 and 4 of the pyrrolidine ring include (2S, 4R), (2s, 4S), (2R, 4S), and (2R, 4R). For example, when the compound (I) having (2S, 4R) carbons at positions 2 and 4 of the pyrrolidine ring is used as a starting material, the compound (II) having (2S, 4R) carbons at positions 2 and 4 of the pyrrolidine ring is formed, and the compounds (III) and (IV) each having (2s, 4S) carbons at positions 2 and 4 of the pyrrolidine ring, respectively, are produced. Similarly, when the (2R, 4S)-compound (I) is used, the (2R, 4S)-compound (II) is formed, and the (2R, 4R)-compounds (III) and (IV), respectively, are obtained.

DETAILED DESCRIPTION OF PREFERRED EMBODIMENTS

The present invention provides novel processes for producing asymmetric synthesis catalysts, phosphinopyrrolidine compounds having the general formula (IV), novel compounds having the general formula (II) and/or novel intermediate compounds having the general formula (III) obtainable by said processes.

The aforementioned $R^1$ and R are independently protecting groups for an imino group. The protecting groups for an imino group are those conventionally used in the general organic synthesis field. The protecting groups used herein can be any without limitation as long as they do not adversely inhibit reaction. The imino protecting groups are those which are stable under ordinary reaction conditions but readily removable either under special conditions or by action with reagents, or those which are known to be capable of protecting selectively only an imino group of concern. The imino protecting groups may also include those which are conventionally used with regard to peptides, nucleic acids and saccharides. The imino protection includes protection with t-butylmethylsilyl derivatives, triaralkylsilyl derivatives such as tribenzylsilyl derivatives, or acyl groups, etc.

$R^1$ and R can be (1) a group having an intervening carbonyl group or (2) a group having an intervening sulfur atom. The protecting group for an imino group includes an optionally substituted or unsubstituted alkylcarbonyl group such as formyl, acetyl, chloroacetyl, dichloroacetyl, trifluoroacetyl, methoxyacetyl, and phenoxyacetyl; an optionally substituted or unsubstituted arylcarbonyl group such as benzoyl, and p-nitro-benzoyl; an alkoxycarbonyl group such as ethoxycarbonyl, $\beta,\beta,\beta$-trichloroethoxycarbonyl, $\beta,\beta,\beta$-tribromoethoxycarbonyl, t-butoxycarbonyl, and trityloxycarbonyl; an optionally substituted or unsubstituted aryloxycarbonyl group such as phenoxycarbonyl, and p-nitrophenoxycarbonyl; an optionally substituted or unsubstituted aralkyloxycarbonyl group such as benzyloxycarbonyl; an optionally substituted or unsubstituted arylsulfonyl group such as benzenesulfonyl, and p-toluenesulfony; an optionally substituted or unsubstituted alkylsulfonyl group such as methylsulfonyl; an optionally substituted or unsubstituted carbamoyl group such as methylcarbamoyl, t-butylcarbamoyl, and phenylcarbamoyl; etc.

For $R^1$ and R, the group having an intervening carbonyl group includes a group having the formula: —CO—$R^a$ wherein $R^a$ is an optionally substituted or unsubstituted hydrocarbon residue; a group having the formula: —COOR$^b$ wherein $R^b$ is an optionally substituted or unsubstituted hydrocarbon residue; a group having the formula: —CONR$^c$R$^d$ wherein $R^c$ and $R^d$ which are identical or different, are independently hydrogen or an optionally substituted or unsubstituted hydrocarbon residue; etc.

The hydrocarbon residues for $R^a$, $R^b$, $R^c$ and $R^d$ include alkyl having 1 to 15 carbon atoms such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, and pentadecyl; alkenyl having 2 to 12 carbon atoms such as vinyl, allyl, 2-methylallyl, 2-butenyl, 3-butenyl, and 3-octenyl; alkynyl having 2 to 12 carbon atoms such as ethynyl, 2-propynyl, and 3-hexynyl; cycloalkyl having 3 to 12 carbon atoms such as cyclopropyl, cyclobutyl, cyclopentyl, cyclohexyl, and cycloheptyl; cycloalkenyl having 3 to 12 carbon atoms; aryl having 6 to 12 carbon atoms such as phenyl, and naphthyl; aralkyl having 7 to 14 carbon atoms such as benzyl, phenethyl, and triphenylmethyl (trityl): etc.

For the "optionally substituted or unsubstituted hydrocarbon residue", one or plural substituents which may be identical or different, may be optionally present. The substituents include alkyl having 1 to 15 carbon atoms; alkenyl having 2 to 12 carbon atoms; alkynyl having 2 to 12 carbon atoms; cycloalkyl having 3 to 12 carbon atoms; aryl having 6 to 12 carbon atoms; aralkyl having 7 to 14 carbon atoms; nitro; hydroxyl; mercapto; oxo; thioxo; cyano; carbamoyl; carboxy (including an alkylcarbonyl group having 1 to 4 carbon atoms such as methoxycarbonyl, and ethoxycarbonyl); sulfo; halogen such as fluorine, chlorine, bromine, and iodine; alkoxy having 1 to 4 carbon atoms such as methoxy, ethoxy, propoxy, isopropoxy, butoxy, isobutoxy and t-butoxy; aryloxy having 6 to 12 carbon atoms such as phenoxy; alkylthio having 1 to 4 carbon atoms such as methylthio, ethylthio, n-propylthio, n-butylthio and t-butylthio; arylthio having 6 to 12 carbon atoms such as phenylthio; alkylsulfinyl having 1 to 4 carbon atoms such as methylsulfinyl and ethylsulfinyl; arylsulfinyl having 6 to 12 carbon atoms such as phenylsulfinyl; alkylsulfonyl having 1 to 4 carbon atoms such as methylsulfonyl and ethylsulfonyl; arylsulfonyl having 6 to 12 carbon atoms such as phenylsulfonyl; amino; acylamino having 2 to 8 carbon atoms such as acetylamino and propionylamino; mono- or di-$C_{1-5}$ alkyl-substituted amino such as methylamino, ethylamino, propylamino, isopropylamino, butylamino, dimethylamino, diethylamino and dipropylamino; cycloalkylamino having 3 to 7 carbon atoms such as cyclohexylamino; arylamino having 6 to 12 carbon atoms such as anilino; acyl having 2 to 8 carbon atoms such as acetyl; arylcarbonyl having 6 to 12 carbon atoms such as benzoyl; etc. For the aforementioned $R^1$ and R, the group having an intervening sulfur atom includes a group having the formula: —S(O)$_n$—R$^e$ wherein $R^e$ is an optionally substituted or unsubstituted hydrocarbon residue and n is an integer of 0, 1 or 2; etc. For $R^e$, the hydrocarbon residue includes those hydrocarbon residues as aforementioned in $R^a$, $R^b$, $R^c$ or $R^d$.

The aforementioned $R^2$ and $R^3$ which are identical or different, are independently protecting groups for a hydroxy group. The protecting groups for a hydroxy group are those conventionally used in the general organic synthesis field. The protecting groups used herein can be any without limitation as long as they do not adversely inhibit reaction. The hydroxy protecting groups are those which are stable under ordinary reaction conditions but readily removable either under special conditions or by action with reagents, or those which are known to be capable of protecting selectively only a hydroxy group of concern. The hydroxy protecting groups may also include those which are conventionally used with regard to peptides, nucleic acids and saccharides. Particularly preferred examples of the hydroxy protecting groups are an optionally substituted or unsubstituted arylsulfonyl such as benzenesulfonyl and p-toluenesulfonyl; an optionally substituted or unsubstituted alkylsulfonyl such as methylsulfonyl; etc., uses of which enable us to conduct efficiently removal of a hydroxy group and phosphination.

The aforementioned $R^2$ and $R^3$ which are identical or different, can be independently a group having an intervening sulfur atom. For $R^2$ and $R^3$, the group having an intervening sulfur atom includes a group having the formula: —$SO_2$—$R^{2a}$ wherein $R^{2a}$ is an optionally substituted or unsubstituted hydrocarbon residue, etc. For $R^{2a}$, the hydrocarbon residue includes those hydrocarbon residues as aforementioned in $R^a$, $R^b$, $R^c$ or $R^d$.

The aforementioned $R^4$ and $R^5$ which are identical or different, are independently an optionally substituted or unsubstituted aromatic hydrocarbon residue. For said $R^4$ and $R^5$, "aromatic hydrocarbon residue" refers to aryl having 6 to 12 carbon atoms such as phenyl, and naphthyl; aralkyl having 7 to 14 carbon atoms such as benzyl, phenethyl, and triphenylmethyl (trityl): etc., as aforementioned for the hydrocarbon residue in $R^a$, $R^b$, $R^c$ or $R^d$. For the "optionally substituted or unsubstituted aromatic hydrocarbon residue", substituents refer to those as aforementioned in the substituents for the "optionally substituted or unsubstituted hydrocarbon residue". Preferred examples of $R^4$ and $R^5$ are unsubstituted aromatic hydrocarbon residues; aromatic hydrocarbon residues which may optionally have one or more substituents (for example, alkyl, alkoxy, mono-, di- or tri-alkyl-substituted amino, halogen, etc.); etc. More preferred examples of $R^4$ and $R^5$ are phenyl; phenyl which may optionally have one or more substituents (e.g., alkyl, alkoxy, mono-, di- or tri-alkyl-substituted amino, halogen, etc.); etc. Particularly, $R^4$ and $R^5$ are preferably, identical and an optionally substituted phenyl such as o-, m- or p-methoxyphenyl, 3,5-dimethyl-4-methoxyphenyl, 4-dimethylaminophenyl and 4-chlorophenyl.

In the process for producing the compound (II) from the compound (I), the metal phosphine compounds used herein include those which are known in the related organic synthesis field to be capable of attacking a substituent: —$OR^3$ for its removal whereby a radical: —$PR^4R^5$ enters in its place. Examples of the metal phosphine compounds are metal phosphine compounds of the formula: $R^4R^5PM$ wherein $R^4$ and $R^5$ are as defined above, and M is a metal atom, and the like. Particularly preferred examples thereof are metal phosphine compounds of the formula: $(R^4)_2PM$ wherein $R^4$ is as defined above, and M is a metal atom, etc. Although the metal phosphine compounds of the formula: $R^4R^5PM$ can be prepared by reacting a corresponding phosphine halide with a metal (e.g., alkali metal such as sodium, lithium and potassium, and the like), reagents commercially available in the art are usually utilized herein conveniently. The metal phosphine compounds include lithium diphenylphosphine ($Ph_2$—Li), sodium diphenylphosphine ($Ph_2P$—Na), etc.

In the processes both for producing the compound (II) from the compound (I) and for producing the compound (III) from the compound (II), the boron compounds which are identical or different, are borane ($BH_3$), coordination complexes of borane with tetrahydrofuran ($BH_3.THF$), coordination complexes of borane with dimethylsulfide ($BH_3.S(CH_3)_2$), borane complexes with amines wherein the amines are selected from the group consisting of $NH_3$, t-butylamine, dimethylamine, trialkylamine, morpholine, pyrrolidine, piperidine, pyridine, etc., borane derivatives (for example, tertiary hexylborane or thexylborane (($CH_3)_2CHC(CH_3)_2BH_2$; $ThxBH_2$), monoisopinocamphenylborane ($IpcBH_2$), diisopinocamphenylborane ($Ipc_2BH$), 9-borabicyclo[3.3.1]nonane (9-BBN), disiamylborane ([($CH_3)_2CHCH(CH_3)]_2BH$; $Sia_2BH$), dicyclohexylborane ($Cy_2BH$), catecholborane, etc.), complexes of the borane derivatives with THF, $S(CH_3)_2$ or amines, etc. Preferred examples thereof are $BH_3$, $BH_3.THF$, $BH_3.S(CH_3)_2$, borane-morpholine complex salts, borane-pyrrolidine complex salts, borane-piperidine complex salts, borane-trialkylamine complex salts, etc. More preferred examples thereof are $BH_3.THF$, $BH_3.S(CH_3)_2$ and the like. The boron compounds are usually used for reaction in the form of a solution in aprotic solvents such as tetrahydrofuran (THF) and diethyl ether. In case of borane complexes with amines, they can also be employed in the form of a solution in ordinary solvents including alcohol, water, etc. Suitably tetrahydrofuran solution of $BH_3.THF$ or $BH_3.S(CH_3)_2$ is used. For the boron compounds, reagents commercially available in the art are usually utilized herein conveniently.

The compounds of the formula (I) can be prepared by techniques as disclosed in U.S. Pat. No. 4,879,389 or those similar thereto and the like.

In the processes both for producing the compound (II) from the compound (I) and for producing the compound (III) from the compound (II), reaction is preferably conducted in a suitable solvent. Such solvents are aprotic ones including ethers such as tetrahydrofuran, diethyl ether, isopropyl ether and methyl t-butyl ether, aromatic hydrocarbons such as benzene, toluene and xylene, N,N-dimethylformamide (DMF), etc. These solvents can be readily used alone or in the form of a mixture of 2 or more species in suitable ratios.

In the process for producing the compound (II), the metal phosphine compound may be reacted with the boron compound either stepwise or simultaneously, thereby selectively replacing a primary hydroxyl radical with a phosphino radical. In this process, the reaction is preferably conducted at a very low temperature. The reaction temperature is from about −70° C. to +10° C., preferably from about −60° C. to −20° C., more preferably from about −50° C. to −30° C., or further more preferably at about −40° C.

In a typical process, the reaction is performed according to the following scheme:

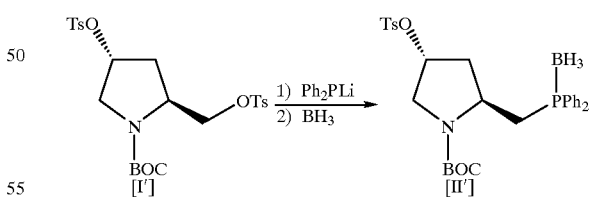

In the above process, the ditosylate compound [I'] is reacted with lithium diphenylphosphine in tetrahydrofuran at about −40° C., thereby replacing its primary hydroxyl radical with a diphenylphosphino radical. Thereafter, the action of borane leads to formation of the compound [II']. For the above process, typical reaction conditions are as follows:

1) solvent: tetrahydrofuran, isopropyl ether, diethyl ether, methyl tert-butyl ether, benzene, toluene, xylene, DMF
2) reagent: $Ph_2P$—Li, $Ph_2P$—Na, $Ph_2P$—K, etc.

3) temperature: −40° C., −70 to +10° C.

4) time: 16 hrs, 2 to 24 hrs

In the above process, the resultant compound [II'] produced in the diphenylphosphination step is protected by complexing its phosphorous atom with the boron atom of borane. Therefore, no oxidized compounds would be formed as by-products from oxidation in contact with oxygen in air. Lithium diphenylphosphine is reacted with borane either stepwise or simultaneously, thereby selectively replacing a primary hydroxyl radical with a phosphino radical. In the aforementioned Process Scheme, it is depicted that the compounds (I) having (2S, 4R) carbons at positions 2 and 4 of the pyrrolidine ring are used as starting materials. It goes without saying that compounds each having other stereoconfigurations can be used herein.

For the metal dicyclohexylphosphine compounds used in the process for producing the compound (III) from the compound (II), compounds of dicyclohexylphosphine with alkali metals such as sodium, lithium and potassium, and other species, can be suitably employed. The metal dicyclohexylphosphine compounds can be prepared by reacting a corresponding phosphine halide with a metal (e.g., sodium, lithium and potassium, and the like). For the metal dicyclohexylphosphine compounds, reagents commercially available in the art are usually utilizable herein conveniently. Such metal phosphine compounds include, for example, lithium dicyclohexylphosphine ($Cy_2P$—Li), sodium dicyclohexylphosphine ($Cy_2P$—Na), etc. In the process for producing the compound (III) from the compound (II), the metal dicyclohexylphosphine compound is reacted with the boron compound preferably at a temperature higher than in the process for producing the compound (II), thereby replacing a secondary hydroxyl radical with a phosphino radical. In this process, the reaction can usually be conducted at from low temperature to ambient temperature. Examples of the reaction temperature are from about 0° C. to 40° C., preferably from about 5° C. to 30° C., more preferably from about 10° C. to 25° C., or further more preferably about 20° C.

In a typical process, the reaction is performed according to the following scheme:

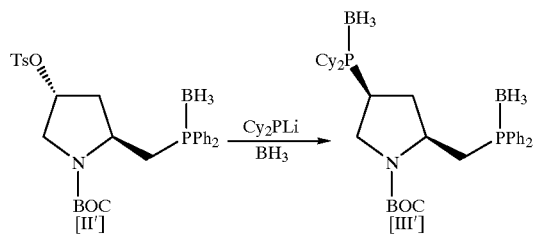

In the above process, the diphenylphosphine-borane complex compound [II'] is reacted with lithium dicyclohexylphosphine and borane in tetrahydrofuran to form the compound [III'] wherein a secondary hydroxyl radical is replaced with dicyclohexylphosphino radical. For the above process, typical reaction conditions are as follows:

1) solvent: tetrahydrofuran, isopropyl ether, diethyl ether, methyl tert-butyl ether, benzene, toluene, xylene, DMF 2) reagent: $Cy_2P$—Li, $Cy_2P$—Na, $Cy_2P$—K, etc.

3) temperature: 20° C., 0 to 40° C.

4) time: 16 hrs, 2 to 24 hrs

In the above process, the resultant compound [III'] produced in the dicyclohexylphosphination step is protected by complexing its phosphorous atom with the boron atom of borane. Therefore, no oxidized compounds would be formed as by-products from oxidation in contact with oxygen in air. In the aforementioned Process Scheme, it is depicted that the compounds (II) having (2S, 4R) carbons at positions 2 and 4 of the pyrrolidine ring are used as starting materials and, as a result, the compounds (III) having (2S, 4S) carbons at positions 2 and 4 of the pyrrolidine ring are formed. It goes without saying that compounds each having other stereoconfigurations can be used herein, leading to products each having corresponding stereoconfigurations thereto. For the process for producing the compound (IV) from the compound (III), treatments capable of removing a boron compound complexed on its phosporous atom can be adapted without limitation. Reagents which can be used in these treatments include acids such as $CH_3SO_3H$, $CF_3SO_3H$, $HBF_4 \cdot O(CH_3)_2$, Lewis acids, etc. Lewis acids are capable of binding with a pair of electrons. For the reagents, those which are known to be capable of cleaving phosphorous-boron bonds can be adapted to be employed in the present invention. The protecting group for an imino group on the nitrogen atom of the pyrrolidine ring in the compound (IV) may be either eliminated, leading to displacement with hydrogen, or retained as it is.

In a typical process, the reaction is performed according to the following scheme:

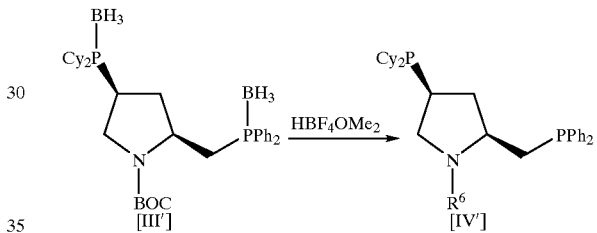

In the above process, the compound [III'] is reacted with $HBF_4OMe_2$ in dichloromethane, leading to deboranation, whereby the compound [IV'] is formed in high yield. Typically, in the above process $R^6$ is hydrogen or t-butoxycarbonyl. For the above process, typical reaction conditions are as follows:

1) solvent: dichloromethane, dichloroethane, benzene, toluene 2) reagent: $HBF_4OMe_2$, $CH_3SO_3H$, $CF_3SO_3H$ 3) temperature: 20° C., −5° C. to 40° C.

4) time: 12 hrs, 1 to 24 hrs

The borane complexed with the phosphorous atom of the diphenylphosphino group can be eliminated with secondary amines such as morpholine and diethylamine, while the borane complexed with the phosphorous atom of the dicyclohexylphosphino group is not removed. The borane on the dicyclohexylphosphino group can be, however, readily eliminated with the aforementioned acids and Lewis acids. In the aforementioned Process Scheme, it is depicted that the compounds (IV) having (2S, 4S) carbons at positions 2 and 4 of the pyrrolidine ring are derived from the compounds (III) having (2S, 4S) carbons at positions 2 and 4 of the pyrrolidine ring (the stereoconfiguration each of carbons at positions 2 and 4 of the pyrrolidine ring is retained). It goes without saying that compounds each having other stereoconfigurations can be used herein, leading to products each having corresponding stereoconfigurations thereto.

When the desired product compounds (IV) wherein $R^6$ is hydrogen, etc. are obtained, the imino group can be protected if required. The imino group can be protected by using reactive ester compounds of the aforementioned protecting groups for the imino group, such as carbonate esters, halogen derivatives, and acid anhydrides thereof. The protection may be conducted by conventionally known techniques in the art, for example, by methods as disclosed in U.S. Pat. No. 4,879,389 or modifications thereof. Thus, the desired compounds (V) are obtained.

The reaction scheme according to the present invention is generally depicted below, together with typical agents therefor:

PROCESS FLOWCHART

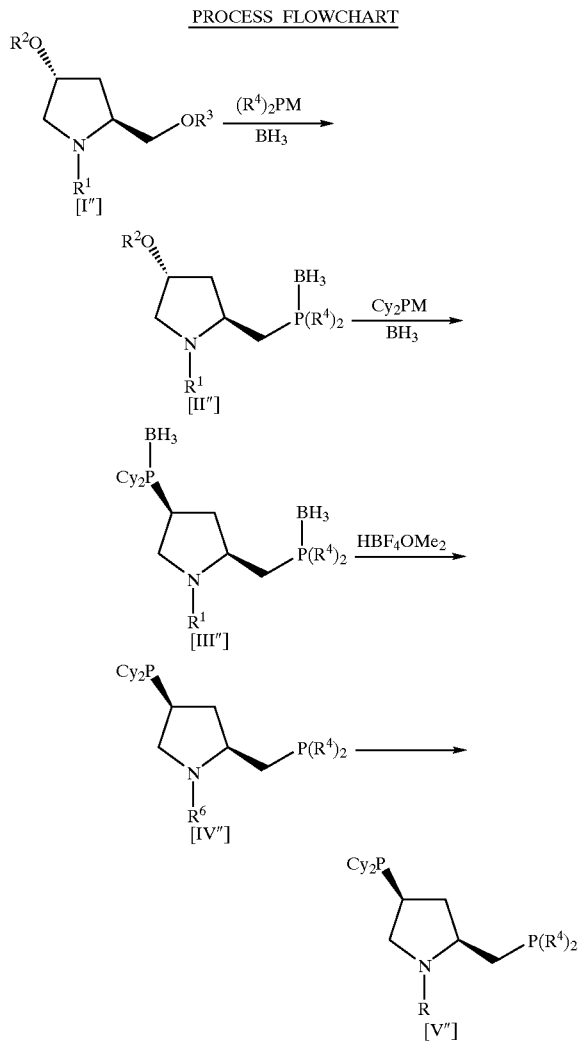

Typical substituents for the compounds described in the above flow-chart include, for example:

$R^1$: a protecting group for an imino group (t-butoxycarbonyl, methoxycarbonyl, benzyloxycarbonyl, benzoyl, p-methoxybenzyloxycarbonyl, acetyl, t-butylcarbonyl, methylcarbamoyl, t-butylcarbamoyl, etc.);

$R^2$ and $R^3$: a protecting group for a hydroxy group (tosyl, mesyl, etc.) wherein $R^2$ and $R^3$ may be same or different;

$R^4$: an optionally substituted or unsubstituted phenyl group wherein substituents are alkoxy, alkyl, halogen, substituted amino, etc. (examples of substituents thereon are o-, m- or p-methoxy, 3,5-dimethyl-4-methoxy, 4-dimethylamino, 4-chloro, etc.);

$R^6$: hydrogen or a protecting group for an imino group (t-butoxycarbonyl, methoxycarbonyl, benzyloxycarbonyl, benzoyl, p-methoxybenzyloxycarbonyl, acetyl, t-butylcarbonyl, methylcarbamoyl, t-butylcarbamoyl, etc.); and R: a protecting group for an imino group (t-butoxycarbonyl, methoxycarbonyl, benzyloxycarbonyl, benzoyl, p-methoxybenzyloxycarbonyl, acetyl, t-butylcarbonyl, methylcarbamoyl, t-butylcarbamoyl, etc.).

The solvates each of the compounds (II), (III) and (IV) include, for example, solvates or adducts with aprotic solvents including ethers such as tetrahydrofuran, diethyl ether, isopropyl ether and methyl t-butyl ether, etc.

In the processes according to the present invention, the compounds (II), (III) and (IV) can be used in next steps without further isolation and/or separation, respectively, and optionally the R radical can be introduced on the N atom of their pyrrolidine ring, for example, by methods as disclosed in U.S. Pat. No. 4,879,389 or those analogous thereto.

By utilizing the aforementioned various embodiments, it is possible to produce not only phosphinopyrrolidine compounds useful for chiral ligands of catalysts in asymmetric synthesis but also novel phosphinopyrrolidine compounds (the compounds (II) and (III)). Particularly, the present phosphinopyrrolidine compounds which are products of the present invention are useful in formation of metal complex catalysts such as rhodium complex catalysts to which said phosphinopyrrolidine compounds are coordinated and said metal complex catalysts are also useful in asymmetric reduction. Since such suitable phosphinopyrrolidine compounds are optically active ones such as members each having (2S, 4S) carbons at positions 2 and 4 of the pyrrolidine ring, it is preferred that optically active compounds with specific stereoconfigurations can be adapted to be employed as starting materials in production of corresponding target products as optically active species. For example, the present phosphinopyrrolidine compounds can be adapted to be employed in asymmetric syntheses including synthesis of D-pantolactone from ketopantolactone, by techniques as disclosed in U.S. Pat. No. 4,879,389 or analogues thereto. The present invention further provides a variety of techniques such as efficient and advantageous asymmetric synthesis systems.

While the present invention has been described specifically in detail with reference to certain embodiments and examples thereof, it would be apparent that it is possible to practice it in other forms without limitation. In light of the disclosure, it will be understood that various modifications and variations are within the spirit and scope of the appended claims. For terms (words) and/or abbreviations used in the specification and in the drawings, they must conform with the meanings of the terms which are commonly or conventionally used in the art. Abbreviations as listed below are principally used hereinbelow:

Cy: cyclohexyl
Ts: tosyl
Me: methyl
BOC: t-butoxycarbonyl
Ph: phenyl
t-Bu: t-butyl

EXAMPLES

Described below are examples of the present invention which are provided only for illustrative purposes, and not to limit the scope of the present invention. In light of the present disclosure, numerous embodiments for carrying out the invention that are obvious to those of skill in the art are intended to be within the scope of the claims.

Example 1
Preparation of (2S,4R)-N-tert-butoxycarbonyl-4-tosyloxy-2-diphenylphosphinomethylpyrrolidine-borane complex salt [II']

Diphenylphosphine (0.35 ml, 2.0 mmol) was dissolved in 3 ml of tetrahydrofuran. To the diphenylphosphine solution was added 1.27 ml (2.0 mmol) of hexane solution containing n-butyl lithium (1.57M) dropwise at −40° C. under argon atmosphere and the mixture was stirred for 15 minutes at the same temperature. Thereafter, the resulting red solution was slowly added to a solution of (2S,4R)-N-tert-butoxycarbonyl-4-hydroxy-2-prolinol ditosylate [I'] (1.05 g, 2.0 mmol) in tetrahydrofuran (5 ml) dropwise. After completion of the addition, the mixture was stirred for 16 hours at the same temperature and evaporated under vacuum. Then to the mixture was added 2.0 ml (2.0 mmol) of tetrahydrofuran solution containing borane (1.0M) dropwise along with ice cooling under argon atmosphere. After stirring for 15 minutes at the same temperature, the mixture was further stirred for 3 hours at room temperature, and evaporated in vacuo. To the resultant residue was added water along with ice cooling and the aqueous mixture was extracted with toluene. The toluene layer was washed with aqueous saturated sodium bicarbonate, and aqueous saturated sodium chloride, respectively, and dried over anhydrous sodium sulfate. After distilling off the solvent, the residue was subjected to purification using chromatography on silica gel (eluant, toluene: ethyl acetate=10:1) to afford white crystals of the product compound [II'] (0.7 g, 67%), mp. 135 to 138° C.

$^1$H-NMR(CDCl$_3$) ppm; 1.42 (9H, s, t—Bu—), 2.45 (3H, s, P—CH$_3$), 3.19 to 4.21 (7H, m, —CH$_2$NCH(CH$_2$)CH$_2$—), 4.89 (1H, brs, TsO—CH), 7.15 to 7.92 (14H, m, Ar—H)

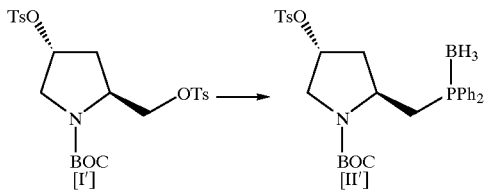

Example 2
Preparation of (2S,4S)-N-tert-butoxycarbonyl-4-dicyclohexylphosphino-2-diphenylphosphinomethylpyrrolidine-diborane complex salt [III']

Dicyclohexylphosphine (59 mg, 0.3 mmol) was dissolved in 2 ml of tetrahydrofuran (THF). To the dicyclohexylphosphine solution was added 0.3 ml (0.3 mmol) of THF solution containing borane (1.0M) dropwise along with ice cooling under argon atmosphere and the mixture was stirred for 4 hours. Thereafter, to the mixture was added 0.25 ml (0.4 mmol) of hexane solution containing n-butyl lithium (1.63M) dropwise along with ice cooling, and the resultant mixture was stirred for 15 minutes at the same temperature. To the mixture was then added slowly dropwise a solution of (2S,4R)-N-tert-butoxycarbonyl-4-tosyloxy-2-diphenylphosphinomethylpyrrolidine-borane complex salt [II'] (111 mg, 0.2 mmol) dissolved in 2 ml of THF and the resultant mixture was stirred for 30 minutes along with ice cooling and further overnight at room temperature. After distilling off the solvent under vacuum, water was added to the residue, followed by extraction with toluene. The toluene layer was washed with aqueous saturated sodium bicarbonate, and aqueous saturated sodium chloride, respectively, and dried over anhydrous sodium sulfate. After drying, the solvent was distilled off and the residue was subjected to purification using chromatography on silica gel (eluant, toluene: ethyl acetate=10:1) to afford crystals of the product compound [III'] (34 mg, 50%), mp. 101 to 104° C.

$^1$H-NMR(CDCl$_3$) ppm: 1.02 to 1.95 (22H, m, —Cy—H), 1.47(9H, s, t—Bu—), 2.95 to 4.31 (8H, m, —CHCH$_2$NCH(CH$_2$)CH$_2$—), 7.12 to 7.91 (10H, m, Ph—H)

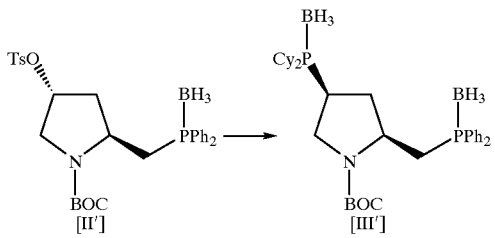

Example 3
Preparation of (2S,4S)-4-dicyclohexylphosphino-2-diphenylphosphinomethylpyrrolidine [IV']

To a solution of (2S,4S)-N-tert-butoxycarbonyl-4-dicyclohexylphosphino-2-diphenylphosphinomethylpyrrolidine-diborane complex salt [III'] (60 mg (0.1 mmol) dissolved in 2 ml of methylene chloride was added 0.12 ml (1.0 mmol) of HBF$_4$OMe$_2$ along with ice cooling and the mixture was then stirred for 12 hours at room temperature, followed by addition of 2 N aqueous sodium hydroxide. The mixture was extracted with toluene, partitioned and concentrated to dryness to afford the product compound [IV'] (42 mg, 90%)

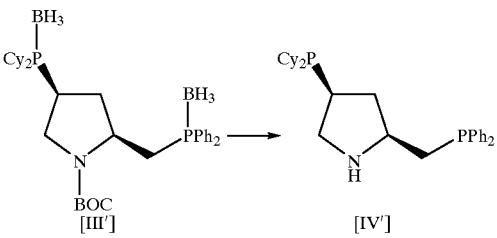

Example 4
Preparation of (2S,4S)-N-tert-butoxycarbonyl-4-dicyclohexylphosphino-2-diphenylphosphinomethylpyrrolidine (BCPM)

To a solution of (2S,4S)-4-dicyclohexylphosphino-2-diphenylphosphinomethylpyrrolidine [IV'] (46 mg, 0.1 mmol) dissolved in 1 ml of methylene chloride was added a solution of di-tert-butylcarbonate (24 mg, 0.11 mmol) dissolved in 11 mg (0.11 mmol) of triethylamine and 2 ml of methylene chloride and the resultant mixture was stirred for 2 to 3 hours at room temperature under nitrogen atmosphere. The reaction solution was concentrated under vacuum to afford white crystalline BCPM (50 mg, 86%), mp. 171 to 174° C.

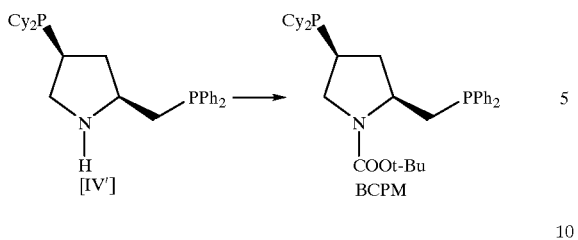

INDUSTRIAL APPLICABILITY

The improved processes are of extremely simple steps and can avoid reaction at elevated temperatures (e.g., 150° C.) and pressures (e.g., 150 atm) such as reduction of benzene nuclei to cyclohexyl groups whereby special manufacturing facilities are unnecessary. It is, therefore, possible to produce advantageously the phosphinopyrrolidine compounds, readily, efficiently and unexpensively from the viewpoint of industry, which are chiral ligands of useful and effective catalysts for asymmetric syntheses. The present invention enables us to prepare the desired phosphinopyrrolidine compounds (chiral ligands for catalysts useful in asymmetric syntheses) by using merely quite less steps than in the prior art. The application of asymmetric syntheses employing the phosphinopyrrolidine compounds may extend. A variety of optically active compounds which are hardly prepared in the prior art can be produced by a diversity of asymmetric syntheses using the present phosphinopyrrolidine compound agents.

What is claimed is:

1. A process for producing a compound having formula (IV):

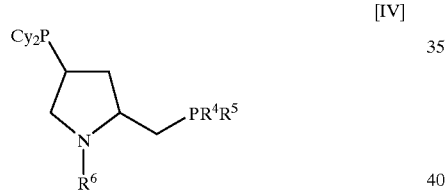

wherein Cy is cyclohexyl, $R^4$ and $R^5$ are identical or different and are independently a substituted or unsubstituted aromatic hydrocarbon, and $R^6$ is hydrogen or a protecting group for an imino group, which comprises (i) reacting a compound having formula (I):

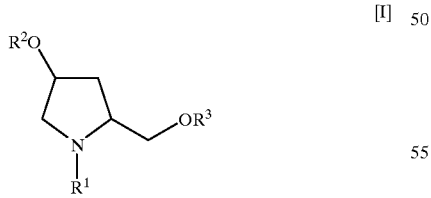

wherein $R^1$ is a protecting group for an imino group, $R^2$ and $R^3$ are identical or different and are independently a protecting group for a hydroxy group, with a metal phosphine compound and a boron compound to form a compound having formula (II):

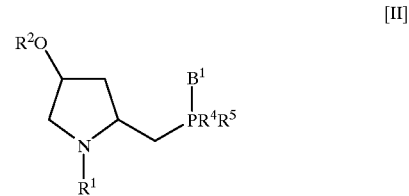

wherein $R^1$, $R^2$, $R^4$ and $R^5$ are defined above and $B^1$ is a first boron compound, (ii) reacting compound (II) with a metal dicyclohexylphosphine compound and a boron compound to form a compound having formula (III):

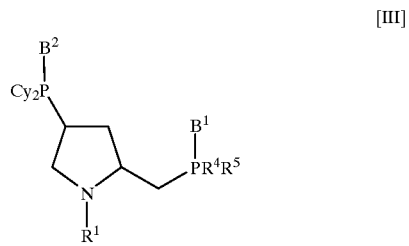

wherein Cy, $R^1$, $R^4$, $R^5$ and $B^1$ are defined above and $B^2$ is a second boron compound which is identical or different to $B^1$, (iii) removing the boron compounds $B^1$ and $B^2$ from compound (III) using a reagent capable of cleaving phosphorous-boron bonds, and (iv) retaining $R^1$, or replacing $R^1$ with hydrogen, to obtain compound (IV).

2. A compound having formula (III):

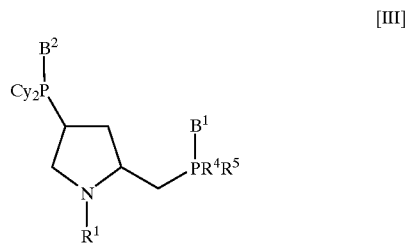

wherein Cy is cyclohexyl, $R^1$ is a protecting group for an imino group, $R^4$ and $R^5$ are identical or different and are independently a substituted or unsubstituted aromatic hydrocarbon, and $B^1$ and $B^2$ are first and second boron compounds, respectively, which are identical or different, or a solvate thereof.

3. A process for producing a compound having formula (III):

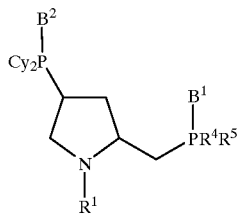

wherein Cy is cyclohexyl, $R^1$ is a protecting group for an imino group, $R^4$ and $R^5$ are identical or different and are independently a substituted or unsubstituted aromatic hydrocarbon, and $B^1$ and $B^2$ are first and second boron compounds, respectively, which are identical or different, which comprises (i) reacting a compound having formula (II):

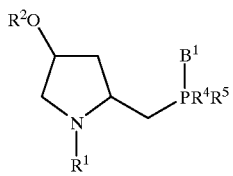

wherein $R^2$ is a protecting group for a hydroxy group, and $R^1$, $R^4$, $R^5$ and $B^1$ are defined above, with a metal dicyclohexylphosphine compound and a boron compound to form the compound (III).

4. A compound having formula (II):

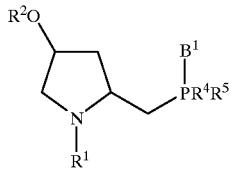

wherein $R^1$ is a protecting group for an imino group, $R^2$ is a protecting group for a hydroxy group, $R^4$ and $R^5$ are identical or different and are independently a substituted or unsubstituted aromatic hydrocarbon, and $B^1$ is a boron compound, or a solvate thereof.

5. A process for producing a compound having formula (II):

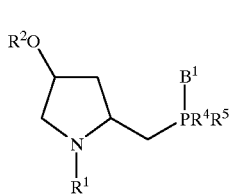

wherein $R^1$ is a protecting group for an imino group, $R^2$ is a protecting group for a hydroxy group, $R^4$ and $R^5$ are identical or different and are independently a substituted or unsubstituted aromatic hydrocarbon, and $B^1$ is a boron compound, which comprises (i) reacting a compound having formula (I):

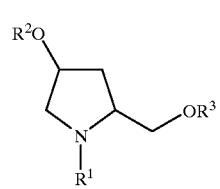

wherein $R^1$ and $R^2$ are defined above, $R^3$ is identical or different to $R^2$ and is independently a protecting group for a hydroxy group, with a metal phosphine compound and a boron compound to form the compound (II).

6. A process for producing a compound having formula (IV):

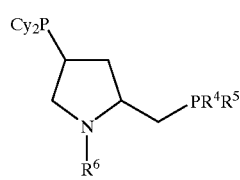

wherein Cy is cyclohexyl, $R^4$ and $R^5$ are identical or different and are independently a substituted or unsubstituted aromatic hydrocarbon, and $R^6$ is hydrogen or a protecting group for an imino group, which comprises (i) removing boron compounds $B^1$ and $B^2$ from a compound having formula (III):

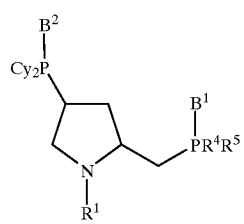

wherein $R^1$ is a protecting group for an imino group, $B^1$ and $B^2$ are first and second boron compounds, respectively, which are identical or different, and $R^4$ and $R^5$ are defined above, using a reagent capable of cleaving phosphorous-boron bonds, and (ii) retaining $R^1$, or replacing $R^1$ with hydrogen, to obtain compound (IV).

* * * * *